United States Patent
Kloepper et al.

(10) Patent No.: US 6,524,998 B1
(45) Date of Patent: Feb. 25, 2003

(54) BIOLOGICAL COMPOSITIONS AND METHODS FOR ENHANCING PLANT GROWTH AND HEALTH AND PRODUCING DISEASE-SUPPRESSIVE PLANTS

(75) Inventors: Joseph W. Kloepper, Auburn, AL (US); Rodrigo Rodriguez-Kabana, Auburn, AL (US); Donald S. Kenney, Denton, TX (US)

(73) Assignees: Auburn University, AL (US); Gustafson, LLC, TX (US)

( * ) Notice: Subject to any disclaimer, the term of this patent is extended or adjusted under 35 U.S.C. 154(b) by 0 days.

(21) Appl. No.: 09/511,359

(22) Filed: Feb. 23, 2000

Related U.S. Application Data

(60) Provisional application No. 60/122,311, filed on Mar. 1, 1999, and provisional application No. 60/139,850, filed on Jun. 18, 1999.

(51) Int. Cl.[7] .......................... A01N 43/08; A01N 63/00
(52) U.S. Cl. ........................................ 504/100; 504/117
(58) Field of Search ................................. 504/117, 100

(56) References Cited

U.S. PATENT DOCUMENTS 5,628,144 A * 5/1997 Eastin ............................ 47/58

OTHER PUBLICATIONS

Benhamou et al. "Induction of resistance against Fusarium wilt of tomato by combination of chitosan with an endophytic bacterial strain: ultrastructure and cytochemistry of the host response" Planta 204(2):153–168, Feb. 1998.*

Lyon et al. "Novel disease control compounds: the potental to 'immunize' plants against infection" Plant Pathology. 44:407–427, 1995.*

Benhamou, Nicole. "Elicitor-induced plant defence pathways" Trends in Plant Science. 1(7):233–240, 1996.*

Hadwiger et al. "Chitosan, a natural regulator in plant-fungal pathogen interactions, increases crop yields" in Chitin, Chitosan, and Related Enzymes. John Zikakis, ed. NY:Academic Pr. Inc. P. 291–302, 1984.*

Raupach et al. "Mixtures of Plant Growth-Promoting Rhizobacteria Enhance Biological Control of Multiple Cucumber Pathogens". Phytopathology. 88(11):1158–1164, 1998.*

* cited by examiner

*Primary Examiner*—S. Mark Clardy
(74) *Attorney, Agent, or Firm*—Schnader Harrison Segal & Lewis LLP

(57) ABSTRACT

The invention accelerates the growth of all types of plants, i.e. tomato, cucumber, bell pepper, tobacco, horticultural crops, and others, and increases plant health. The invention is designed to increase the rate of seedling growth in the soil or in the greenhouse; and produce seeds having a coating imparting resistance to disease, thereby decreasing the time required to produce transplants in seedling greenhouses prior to transplanting into agricultural fields; and develop "disease-suppressive" transplant plugs, which are protected for a time from multiple diseases through combined mechanisms of stimulated plant defense and increased activity of indigenous antagonistic microorganisms on plant roots. Compositions and methods of use are provided.

33 Claims, No Drawings

BIOLOGICAL COMPOSITIONS AND METHODS FOR ENHANCING PLANT GROWTH AND HEALTH AND PRODUCING DISEASE-SUPPRESSIVE PLANTS

CROSS-REFERENCE TO RELATED APPLICATIONS

This application is based on provisional application Ser. No. 60/122,311, filed Mar. 1, 1999, and provisional application Ser. No. 60/139,850, filed Jun. 18, 1999 entitled: Biological Preparations for Enhanced Plant Growth and Health". This application claims the benefit of the filing dates of the above-identified provisional applications, which are incorporated herein by reference in its entirety.

BACKGROUND OF THE INVENTION

Field of Invention

The invention relates to improvements in plants. In particular, the invention relates to improved biological compositions which are effective to increase the growth rate of seedlings and develop systemic disease immunity in plants and to control soil nematodes. The invention relates also to seeds treated with the composition and to the treated seedlings and plants.

Organic Amendments and Chitin

Naturally occurring nematode suppressiveness has been reported for several agricultural systems (Stirling et al., 1979, Kerry, 1982, Kluepfel et al., 1993,), but suppressiveness can also be induced by crop rotation with antagonistic plants such as switchgrass (*Panicum virgatum*) (Kokalis-Burelle et al., 1995) and velvetbean (*Mucuna deeringiana*) (Vargas et al., 1994) or organic amendments including pine bark (Kokalis-Burelle et al., 1994), hemicellulose (Culbreath et al., 1985), and chitin (Mankau and Das, 1969, Spiegel et al., 1986, Rodríguez-Kábana and Morgan-Jones, 1987). A major component of the suppressiveness of chitin amendments is believed to be biotic, and several reports confirm increased numbers of nematode antagonistic microorganisms associated with chitin-induced suppressive soils (Godoy et al., 1983, Rodríguez-Kábana et al., 1984). Extensive work has been done over the past years on fungi associated with chitin amendments (Godoy et al., 1983, Rodríguez-Kábana et al., 1984), while less information is available on bacterial community structure and the role of bacteria in chitin-induced suppressiveness.

Chitin, a glucosamine polysaccharide, is a structural component of some fungi, insects, various crustaceans and nematode eggs. In egg shells of tylenchoid nematodes, chitin is located between the outer vitelline layer and the inner lipid layer and may occur in association with proteins (Bird and Bird, 1991). The breakdown of this polymer by chitinases can cause premature hatching which results in fewer viable juveniles (Mercer et al., 1992). In the soil, chitinases are produced by some actinomycetes (Mitchell and Alexander, 1962), fungi (Mian et al., 1982), and bacteria (Ordentlich et al., 1988, Inbar and Chet, 1991), but chitinases are also released by many plants as part of their defense mechanism against various pathogens (Punja and Zhang, 1993) and plant-parasitic nematodes (Roberts et al., 1992). Chitinases depolymerize the chitin polymer into N-acetylglucosamine and chitobiose. Further microbial activity results in the deamination of the sugar and accumulation of ammonium ions and nitrates (Rodríguez-Kábana et al., 1983). Nematicidal concentrations of ammonia in association with a newly formed chitinolytic microflora are believed to cause nematode suppressiveness (Mian et al., 1982, Godoy et al., 1983). Benhamou et al. (1994) have shown that chitosan, the deacetylated derivative of chitin, induces systemic plant resistance against *Fusarium oxysporum* f. sp. *radicis-lycopersici* in tomato when applied as a seed treatment or soil amendment. This suggests that plant defense mechanisms might contribute to the overall nematode suppression.

Changes in one component of the microflora in a community often leads to other changes, and it was recently reported that soil amendment with 1% chitin led to alterations in the taxonomic structure of the bacterial communities of the soil, rhizosphere and endorhiza (Hallmann et al., 1998). Several bacterial species were found in chitin-amended soils and cotton rhizospheres which were not detected in non-amended soils and rhizospheres. Additionally, it was determined that chitin-amended soils selectively influenced the community structure of endophytic bacteria within cotton roots. For example, *Phyllobacterium rubiacearum* was not a common endophyte-following chitin amendment, although its populations in soil were stimulated by chitin. *Burkholderia cepacia* was the dominant endophyte-following chitin amendment but was rarely found among the endophytic community of non-amended plants. Hence, alterations in microbial community structure are associated with the control of nematodes which occurs upon soil amendment with chitin.

Plant Growth-Promoting Rhizobacteria (PGPR)

Plant-associated microorganisms have been extensively examined for their roles in natural and induced suppressiveness of soilborne diseases. Among the many groups of such organisms are root-associated bacteria, which generally represent a subset of soil bacteria. Rhizobacteria are a subset of total rhizosphere bacteria which have the capacity, upon re-introduction to seeds or vegetative plant parts (such as potato seed pieces), to colonize the developing root system in the presence of competing soil microflora. Root colonization is typically examined by quantifying bacterial populations on root surfaces; however, some rhizobacteria can also enter roots and establish at least a limited endophytic phase. Hence, root colonization may be viewed as a continuum from the rhizosphere to the rhizoplane to internal tissues of roots.

Rhizobacteria which exert a beneficial effect on the plant being colonized are termed PGPR. PGPR may benefit the host by causing plant growth promotion or biological disease control. The same strain of PGPR may cause both growth promotion and biological control. Efforts to select and apply PGPR for control of specific soilborne fungal pathogens have been reviewed (Kloepper, 1993; Glick and Bashan, 1997). Among the soilborne pathogens shown to be negatively affected by PGPR are Aphanomyces spp., *Fusarium oxysporum, Gaeumannomyces graminis*, Phytophthora spp., Pythium spp., *Rhizoctonia solani, Sclerotium rolfsii, Thielaviopsis basicola*, and Verticillium spp. In most of these cases, biological control results from bacterial production of metabolites which directly inhibit the pathogen, such as antibiotics, hydrogen cyanide, iron-chelating siderophores, and cell wall-degrading enzymes. Plant growth promotion by PGPR may also be an indirect mechanism of biological control, leading to a reduction in the probability of a plant contracting a disease when the growth promotion results in shortening the time that a plant is in a susceptible state, e.g. in the case where PGPR cause enhanced seedling emergence rate, thereby reducing the susceptible time for pre-emergence damping-off. An alternative mechanism for biological control by PGPR is induced systemic resistance.

Nematode Biocontrol Agents

Many recently published examples of biocontrol of nematodes by antagonists involve use of the non-culturable pathogen *Pasteuria penetrans* (reviewed in Stirling, 1991b). Populations of the pathogen often increase upon continual cropping of crops susceptible to nematodes and may contribute to soil suppressiveness to nematodes in these cases. *P. penetrans* produces resting spores which adhere to the cuticle of nematodes, where they produce a germ tube, penetrate the host, and develop an extensive colonization and digestion of the host nematode. Unfortunately, procedures to produce sufficient spores for inoculative biocontrol studies are laborious, and no practical mass cultivation systems are available (Ciancio, 1995). Nematode-trapping fungi have provided control under greenhouse conditions, however practical control in the field has not been consistently achieved. This result most likely occurs since nematode-trapping capacity of most species is not related to nematode density as would be required for economic control (Stirling, 1991a). Several reports of culturable rhizobacteria as biocontrol agents of nematodes have been published (Becker et al., 1988; Hallmann, et al., 1997; Kloepper et al., 1992; Kluepfel, et al., 1993; Martinez-Ochoa et al., 1997; Oka et al., 1993; Sikora, 1988). While some reductions in nematode damage or populations have been reported upon introduction of bacteria in these model systems, none of the studies present data showing field efficacy at levels which would provide economically practical protection.

Induced Systemic Resistance (ISR) with PGPR

Induced resistance, whereby a plant's natural defenses are triggered by a physical, chemical, or biological agent, has been extensively studied and reviewed (Kuć, 1982; Ross, 1961; Ryals et al., 1996; Sticher et al. 1997; van Loon, 1997). Biological agents which induce resistance are of two general types: those that induce a necrotic lesion on the plant, indicating an incompatible pathogen-host interaction, and those that colonize the plant, usually roots, without visible necrosis. Certain rhizosphere bacteria have been shown to colonize roots of plants resulting in increased plant growth or biological control of plant diseases (reviewed in van Loon et al, 1998). Some PGPR strains, like necrosis-inducing biological agents and chemical inducers, trigger the plant's natural defenses in response to pathogen attack. Unlike necrosis-inducing biological agents and chemical inducers which provide a short-term period of induction, PGPR colonize plant roots, thereby potentially providing an extensive period of induction. Most of these published systems use fluorescent pseudomonads, and the mechanism appears to be distinct from ISR induced by pathogens or chemicals in that pathogenisis-related (PR) proteins typically do not accumulate, and the systemic protection is most typically not dependent upon activation of salicylic acid (Press et al., 1998; reviewed in van Loon et al. 1998).

Research in support of the present invention has studied the phenomenon of PGPR-mediated ISR, and the results indicate the following points. Selected PGPR strains belonging to diverse Gram-positive and Gram-negative genera (including Pseudomonas, Serratia, and Bacillus) can, upon seed treatment or soil drench treatment to plant root systems, reduce the incidence of distally infecting pathogens. Single PGPR strains have been shown to reduce pathogen infection and symptoms of multiple diseases on cucumber and tomato. Cucumber diseases affected under both greenhouse and field studies in multiple years include foliar diseases (angular leaf spot, caused by *Pseudomonas syringae* pv. lachrymans [Liu et al., 1991a & b] and anthracnose [Wei et al., 1996], caused by *Colletotrichurn orbiculare*), systemic wilt diseases (cucurbit wilt, caused by *Erwinia tracheiphila* [Zehnder et al., 1997a & b] and Fusarium wilt, caused by *Fusarium oxysporum* f. sp. cucumerinum [Liu et al. 1991c]), and the systemic viral disease caused by cucumber mosaic virus (CMV) (Raupach et al., 1996; Yao et al., 1997). In the case of cucurbit wilt, disease control is linked to PGPR-mediated reductions in plant preference by the insect vectors, such as the striped and spotted cucumber beetles. In field and greenhouse studies, PGPR treatments led to significant reduction in beetle feeding (Zehnder et al., 1997a) which was associated with PGPR-mediated reductions in cucurbitacin C, a feeding attractant. With tomato, protection has been noted in the greenhouse or field against CMV, bacterial spot, caused by *Xanthomonas axonopodis* pv. vesicatoria; tomato mottle geminivirus, and bacterial speck, caused by *P. syringae* pv. tomato.

Botanical Aromatic Compounds

Another approach for control of nematodes which may lead to at least a limited induction of suppressiveness through microbial activity is the use of selected "botanical aromatic compounds". "Botanical aromatics" are low-molecular weight, volatile plant metabolites, many of which are found in essential oils of plants. When incorporated into soil, the volatile nature of botanical aromatics causes the compounds to act as fumigants. Furfural (2-furfuraldehyde) mixed into soil in greenhouse trials suppressed initial populations of the root-knot nematode *Meloidogyne arenaria* and the number of subsequent galls on squash. Similar protections were observed against *M. incognita* (root-knot nematode) and *Heterodera glycines* (cyst nematode) on soybean (Rodríguez-Kábana et al., 1993). Furfural also reduced root-knot damage of okra and increased yields in a microplot trial (Rodríguez-Kábana et al., 1993). Canullo et al. (1992) demonstrated that soil treatments with furfural reduced damage to the pathogenic fungus *Sclerotium rolfsii* on lentil, although populations of Trichoderma spp. and bacterial antagonists to *S. rolfsii* increased.

In a separate study with cotton, the use of the botanical aromatics furfural, benzaldehyde, and citral reduced populations of *M. incognita* juveniles in soil and on roots (Bauske et al., 1994). These same three botanical aromatics (furfural, citral, and benzaldehyde) have shown potential for control of both fungal pathogens and phytoparasitic nematodes (reviewed in Bauske et al., 1997). Applications of furfural and benzaldehyde to soil cause both quantitative and qualitative shifts in the composition of the soil bacterial community (reviewed Bauske et al., 1997). After decreasing in the first 24 hr after application, bacterial populations increased by 1 week after application and remained higher than in non-treated control soils for 7 weeks. There was a corresponding increase in frequency of *Burkholderia cepacia* in treated soils.

Soler-Serratosa et al. (1996) reported that pre-plant applications of thymol to soil reduced initial and final populations of *M. incognita* and *H. glycines* on soybean. When thymol was combined with benzaldehyde, a synergistic effect on nematode populations occurred. The effects of thymol on nematodes was related to changes in the indigenous soil microflora following treatment, and specifically to an increase in Pseudomonas spp. (Soler-Serratosa et al., 1994).

Contribution of the Invention

Notwithstanding this extensive work, an adequate strategy has been developed that provides satisfactory compositions suitable to treat plants from a very early stage (e.g., seeds or seedlings) to yield fast-growing plants which have a systemic resistance against foliar pathogens and alter the soil microflora to effectively control nematodes. Further alternatives to chemical pesticides and methyl bromide soil fumigation for control of plant diseases are needed. Reducing the pressure and dependence of control of plant diseases on chemical pesticide solutions is highly desired.

Therefore, there is an urgent need, both environmentally and economically, for such compositions and methods of treatment devoid of pesticides and pesticide-like elements. It is evident from the prior art that no previous disclosure nor publication has contemplated the invention in that it is possible to achieve synergistic plant growth promotion and induced systemic resistance with the present invention of PGPR and an organic amendment thereby producing plants having an increased growth rate and systemic disease immunity. This invention contributes to the solution of this need and to the problems confronting this field of art.

RELATED ART

A bibliography of related publications appears prior to the claims section of this document.

BRIEF SUMMARY OF INVENTION

The invention relates broadly to the field of plant growth and development, particularly to methods and compositions for enhancing plant growth and disease resistance. The invention relates to the initiation and promotion of plant growth using a combination of multiple tactics of biological control in soil or in a soil-less plant growth medium for controlling nematodes and foliar pathogens.

The invention also relates to a novel composition of a plant growth medium comprising chitin and nonchitinolytic plant growth-promoting rhizobacteria (PGPR) which creates a synergy in plant growth and disease resistance. Further the invention relates to a novel synergistic method of using either seed treatment or the application to a soil-less potting media composition of a chitinolytic element and bacteria elements for the preparation and development of plants and transplants.

The invention relates to various plant products, such as tomato and cucumber plants obtained from the invention. The invention also relates to various other compositions and plants described further below.

The invention provides several useful embodiments.

The invention provides a composition which comprises at least two PGPR bacterial strains and a chitinolytic compound or a compound of equivalent effect. The plant growth promoting rhizobacteria (PGPR) comprise at least one bacterial strain which can induce systemic plant resistance to plant diseases. The composition further comprises a chitinolytic compound which may have nematode-control activity. At least one of the PGPR bacterial strains in a preferred embodiment is non-chitinolytic. The chitinolytic compound is preferably either an aminated organic compound or an aminated polysaccharide.

Other compositions of the invention may include optional ingredients such as at least one botanical aromatic compound. Usually, a botanical aromatic compound for the present invention will have a low molecular weight and be of a volatile plant metabolite, such as citral, furfural or benzaldehyde. Numerous other compounds which do not detrimentally affect the function of the chitinolytic compound and of the PGPR may be included in the composition.

The invention provides further a method for exposing seeds and growing transplant plugs in soil or a soil-less medium, which includes the biological composition of the invention. Thereafter, the seeds and/or plugs are continued to be exposed and/or grown, respectively, in either the field or in an environment having conditions similar to that of greenhouses. These conditions, like greenhouses, may be environmentally controlled for temperature, light, humidity and the like. Alternatively, these conditions, may be free of such environmental controls. The growing continues under these conditions until a predetermined growth and size is obtained. Thereafter, the resulting plant is transferred to field conditions to continue to grow normally. The resulting plants, from either seeds or plugs, have been observed to have developed a systemic disease resistance, increased growth vigor and other desirable properties.

The method of the invention provides different means for treating a transplant seedling or seed of a target plant with the composition of the invention. One such means is to preferably spray the target seedling with an aqueous composition of the invention so as to promote the exposure and penetration of the constituents of the composition into the target plant. Another means is to expose seedlings or seeds of the target plant to the composition of the invention.

Another embodiment of the invention relates to the improved plants obtained by the invention including plants that exhibit a systemic resistance to infectious diseases, whether the infection is of the root system, the foliage or other parts of the plants.

Plants which may be treated and obtained in accordance with the invention include both monocotyledonous and dicotyledonous plant species including barley, oats, rice, wheat, soybean, corn; melons including cucumber, muskmelon, canteloupe and watermelon; vegetables including beans, pea, peanut; oil crops including canola and soybean; solanaceous plants including tobacco; tuber crops including potato; vegetables including tomato, pepper, cucumber, broccoli, cabbage, cauliflower, lettuce and radish; fruits including strawberry; fiber crops including cotton; other plants including coffee, bedding plants, perennials, woody ornamentals, turf and cut flowers including carnation and roses; sugar cane; containerized tree crops; evergreen trees including fir and pine; deciduous trees including maple and oak; and fruit trees including cherry, apple, pear and orange. In general any plant that is susceptible to plant disease and does respond to the composition of the invention may be treated in accordance with the invention.

Other embodiments of the invention will become apparent hereinafter.

DETAILED DESCRIPTION OF INVENTION

The invention relates to various combinations of biocontrol tactics applied together into soil or plant growth media used for production of plants or transplant plugs. The "tactics" may include mixtures of two or more PGPR strains where one or more can induce plant resistance. These "tactics" may further include organic amendments, which may have nematode-control activity, and "selector compounds", such as botanical aromatic compounds (including thymol, benzaldehyde, citral, furfural, menthol and alpha-terpineol), which alter soil microflora to enhance activity of indigenous antagonistic microorganisms. The invention may also consist of using two of these three tactics, i.e. PGPR mixtures together with organic amendments, but without addition of selector compounds. The invention provides other embodiments further discussed hereinafter.

In accordance with the invention, a novel synergy of biocontrol tactics of a heretofore unidentified composition has been discovered. The composition, in accordance with the invention, initiates and promotes plant growth and synergistically induces systemic disease resistance in plants. The characteristics of the composition are both novel and synergistic. The invention provides a composition comprised of chitinolytic and nonchitinolytic constituents for plant growth and disease resistance. The composition results in a synergy of constituent characteristics including initiation and promotion of plant growth and the inducing of systemic plant disease resistance.

The Composition of the Invention

The composition is comprised of at least one PGPR strain and an organic amendment. The biological PGPR mixture preferably comprises spore preparations of the bacteria. Additionally, in the PGPR mixture, at least one PGPR strain can induce systemic plant resistance to disease. The presence of the bacteria in the mixture is generally on the order of $10^3$ to $10^{10}$ bacteria per seed or per liter of soil-less mix. A preferred embodiment of the invention is where the bacteria presence is approximately $1 \times 10^{10}$ bacteria per liter of soil-less mix and $1 \times 10^8$ bacteria per seed.

Examples of two formulated PGPR strains include but are not limited to *Bacillus sublilis* strain GB03 (available from Gustafson LLC., Plano, Tex. as Kodiak™) and *Bacillus amyloliquefaciens* strain IN937a. Other types of nonchitinolytic bacteria suitable for the composition include: root-colonizing bacteria including the family BACILLIACEAE which is spore-forming and comprises the genera Bacillus, Paenibacillus, Brevibacillus, Virgibacillus, Alicyclobacillus and Aneurinibacillus; fluorescent pseudomonads; isolates of Pseudomonas spp., Serratia spp., Cornynebacterium spp., Enterobacterspp., Arthrobacter spp., and Burkholderia spp.; and benefical fungi such as Trichoderma spp., Gliocladium spp., and others; yeasts, and actinomycetes. Additional examples of the group of bacilli and their spore-forming genera, including Bacillus, are referenced in the "ATCC catalogue of Bacteria", published by the American Type Culture Collection, and are incorporated herein by reference.

The organic amendment is also known as a chitinolytic component as it exhibits nematode-control activity. The chitinolytic component in the composition is in an amount sufficient to cause a chitinolytic effect. The amount of the chitinolytic component present may range from 0.1% to 10.0%. A preferred embodiment of the invention is where the composition is comprised of approximately 2.5% of the chitinolytic component.

Examples of the chitinolytic component include but are not limited to chitin, flaked chitin, and chitosan. The chitinolytic component can also be derived from its precursors which upon hydrolysis or other chemical or biochemical breakdown will yield the chitinolytic component. Preferably, the organic amendment is a glucose polysaccharide. Such precursors are organic natural compounds like pine bark, crab or shrimp shells, soybean meal, cotton seed meal and casein.

A further embodiment of the invention is a composition comprising at least one of the PGPR strains, an organic amendment, and an optional botanical aromatic compound. The optional addition of a botanical aromatic compound, also known as a selector compound, to the primary composition further introduces a fumigant for altering soil microflora. The presence of the fumigant reduces parasitic nematodes and increases antagonists. An example of the botanical aromatic compound includes but is not limited to benzadehyde. Other types of botanical aromatic compounds suitable for the composition include citral. Further optional components include components which do not negatively affect the function of the two principal components of the composition, referred to as non-essential ingredients.

A further embodiment of the invention is a composition comprising the two PGPR strains, an organic amendment, and an optional botanical aromatic compound.

The Method of the Invention

An embodiment of the invention is a method for promoting plant growth and synergistically inducing disease resistance in plants. The method comprises exposing seed to the novel biological composition or growing seedlings in a soil-less potting media containing the novel biological composition, for a period of time sufficient to initiate improved growth and disease-suppressive characteristics. A seed is planted in the soil or in the soil-less media and grown in a greenhouse under conditions previously discussed. By way of example, the biological composition may be incorporated into a soil-less media such as in a styrofoam transplant flat and then seeded. During this growth period, if desired, additional treatments of the composition are provided to the plant in predetermined amounts at predetermined times. Then, if desired, when the seedlings have advanced to an age of approximately four to six weeks, or where the plants are ready for transplant, the plant is transplanted to field conditions or greenhouse conditions where the plant has been observed to continue to grow normally. Further, the plants are then optionally treated with the composition, in which the composition is in either a liquid or solid formn. Preferably, this treatment is in the form of a foliar spray, drench application, drip application or through irrigation where it has been observed that the plants achieve a greater resistance to disease. This optional treatment may also be performed at any time during the growth period. Further, untreated seeds are coated by exposing the seed with the composition, either in a liquid or solid form, preferably in a foliar spray, drench application, drip application or through irrigation. This treatment may be optional, and may additionally be performed at any time to untreated or treated seeds.

Particularly, this method stimulates and promotes plant growth in the early seedling stages which is known to be a difficult stage of plant growth to stimulate with PGPR alone. The method also induces disease resistance systemically in plants to a greater extent than previously achieved in the prior art. The invention also synergistically enables both the stimulation and promotion of plant growth in combination with systemically protecting a plant from disease by exposure to the biological composition.

Further embodiments of the invention provide methods for inhibiting the growth of disease agent *Phytophtora infestans* (a causal agent of late blight disease), *Xanthomonas axonopodis* pv. vesicatoria (a causal agent of bacteria spot disease), *Pseudomonas syringae* pv. lachrymans (a causal agent of angular leaf spot disease), and Fusarium spp. by using the method discussed above and challenging the plant with a treatment of the disease agent. The challenged seedling is then evaluated and the incidence and severity of disease are measured . It has been observed that plants grown under the present invention and challenged with the disease exhibited a significantly greater ability to resist the disease.

The Seed, Seedling and Plant of the Invention

An additional embodiment of the invention is a plant which having been exposed to the composition exhibits the synergistic effects of improved growth in combination with the systemic protection from disease. Seeds, seedling and plants which may be treated and obtained in accordance with the invention include both monocotyledonous and dicotyledonous plant species including barley, oats, rice, wheat, soybean, corn; melons including cucumber, muskmelon, cantaloupe and watermelon; vegetables including beans, pea, peanut; oil crops including canola and soybean; solanaceous plants including tobacco; tuber crops including potato; vegetables including tomato, pepper, cucumber, broccoli, cabbage, cauliflower, lettuce and radish; fruits including strawberry; fiber crops including cotton; other plants including coffee, bedding plants, perennials, woody ornamentals, turf and cut flowers including carnation and roses; sugar cane; containerized tree crops; evergreen trees including fir and pine; deciduous trees including maple and oak; and fruit trees including cherry, apple, pear and orange. In general any seed, seedling or plant that is susceptible to plant disease and does respond to the composition of the invention may be treated in accordance with the invention.

The resulting plant of the present invention exhibits improved plant growth in the early seedling stages, which is known to be a difficult stage of plant growth to stimulate with PGPR alone. The plant further exhibits measurably improved plant physical characteristics such as greater height, weight, vigor, leaflets and leaflet surface area, at growth stages earlier than non-treated, control plants. Similarly, the plant displays less disease than untreated, control plants.

Other Embodiments of the Invention

Further embodiments of the invention include various media for culturing the plants using the composition, in particular tomato, cucumber, and classes previously discussed, and parts thereof which have been developed in accordance with the invention.

Other embodiments of the invention will become apparent in the further detailed description of preferred and other embodiments of the invention.

The term "transplant" as used herein is a term of art used to designate a plant of any age of any variety that is moved from one growing location to another.

The term "transplant plug" as used herein is a plant of any age situated in a contained growth medium in which the plant is prepared to be transplanted or transported from one location to another.

The term "soil-less medium" as used herein is a growth medium comprising peat-based products which may contain perlite, vermiculite, a fertilizer component and other ingredients. Examples of a soil-less medium include readily available products such as "Pro-mix", "Redi-Gro" and "Speedling Mix".

The term "seedling" as used herein is a term of art used to designate a plant of an age ranging from the day of emergence to one year after planting or an age where transplant of the plant occurs and is not limited to or by any plant class. The term also includes "forest seedlings" which can be one year old.

The term "synergy" as used herein is used to designate the resulting action of two or more substances to achieve an effect of which each is individually incapable of achieving.

EXAMPLE 1

Synergy of Tactics

A. Growth Promotion of Tomato

As the first example of the invention, a biological preparation was made containing two PGPR strains together with chitin. Specifically, the biological preparation (termed LS213), which is publicly available, contained *Bacillus subtilis* strain GB03, has been shown to control some diseases by production of iturin antibiotics, and *Bacillus amyloliquefaciens* strain IN937a which was selected for activation of induced resistance. With both of these bacteria, industrial formulations of spores were prepared and were mixed with flaked chitin. The biological preparation was added to soil-less potting media which was used to prepare tomato transplant plugs. Additional treatments consisted of each bacterial strain alone with and without chitin, chitin alone, and a nontreated control. Transplant plugs were grown in transplant trays in the greenhouse and effects on seedling growth were noted. Results are presented in Table 1.

Across all three measurements (vigor, shoot fresh weight, and leaflet surface area), significantly greater seedling growth occurred with LS213 than with the various individual components. This indicates a clear synergy in plant growth promotion by the combination of chitin and the two PGPR strains.

TABLE 1

Results of Example 1A-growth promotion of tomato-synergy of tactics.

| Treatment and components[1] | Vigor[2] | Shoot Fresh Weight (g)[3] | Leaflet surface area (cm$^2$)[4] |
|---|---|---|---|
| Control; no components | 1.4 a | 0.4113 a | 3.22 a |
| LS213; chitin + GB03 + IN937a | 4.9 e | 1.6555 f | 18.37 e |
| Chitin alone | 2.3 b | 0.6088 bc | 6.40 b |
| Chitin + GB03 | 2.9 c | 0.7393 de | 6.69 b |
| Chitin + IN937a | 3.6 d | 0.8255 e | 8.29 c |
| GB03 | 2.4 bc | 0.6393 bc | 7.76 c |
| IN937a | 2.1 b | 0.6821 cd | 7.74 c |
| GB03 + IN937a | 2.1 b | 0.5931 b | 6.57 b |
| LSD (P = 0.05) | 0.53 | 0.088 | 0.84 |

[1]Biological treatments were incorporated into soil-less mix at 1:40 (v/v), placed into Styrofoam transplant flats, and then seeded with tomato cv. Solar Set. There were four replicated flats per treatment. GB03 and IN937a are PGPR strains.
[2]Seedling vigor was rated at 3 weeks after seeding on a scale of 1–5; 1 = poor, 2 = average, 3 = good, 4 = very good, 5 = excellent. Mean of four replications.
[3]Seedling shoot fresh weight. Mean of 4 replications, 10 seedlings per replication.
[4]Largest leaflet surface are (usually from the 4rth or 5$^{th}$ true leaf). Mean of 4 replications, 10 leaflets per replication.
Means followed by different letters are significantly different according to the protected least significance difference (LSD) test at P = 0.05.

B. Induced Resistance on Tomato

Certain of the transplant plugs of the above experiment, those being treated with the control, the chitin alone and the LS213, were transplanted to larger pots immediately after making the measurements of growth shown in Table 1. Ten plants of each treatment type were then challenged with *Phytophthora infestans* (causal agent of late blight disease)

or *Xanthomonas axonopodis* pv. vesicatoria (causal agent of bacterial spot disease). After a predetermined time, the plants were measured for disease resistance. Results of disease development are shown in Table 2.

The highest degree of disease protection against both pathogens occurred with LS213. With bacterial spot, the protection afforded by LS213 was significantly greater than both the nontreated control and the chitin alone treatment. This indicates that the synergy in plant growth promotion noted in Table 1 translates into synergy in disease protection.

TABLE 2

Results of Example 1B-Induced resistance on tomato-synergy of tactics.

| Treatments | % Late blight disease/plant[1] | Bacterial spot lesions/leaflet[2] |
|---|---|---|
| Control | 19.1 b | 22.9 b |
| Chitin | 16.5 a | 22.35 b |
| LS213 | 7.7 a | 11.87 a |
| LSD (P = 0.05) | 9.98 | 2.42 |

[1]Mean of 10 replications, one plant per replication.
[2]Mean of 10 replications, 6 leaflets per plant.

EXAMPLE TWO

Synergy of Tactics

A. Growth Promotion of Tomato and Cucumber

An experiment similar to that described in example 1 was conducted. The components of chitin, GB03 and IN937a were tested in soil-less plant growth medium for effects on seedling growth using tomato and cucumber. Additional measurements of plant growth were conducted as shown in Tables 3 and 4. Results are shown in Table 3 and Table 4.

The results with both tomato (Table 3) and cucumber (Table 4) demonstrate again that there is a clear synergy of tactics for growth promotion. For example, with tomato (Table 3), chitin alone had some growth promotion, causing significant increases, relative to the control, in height, number of leaflets, and leaflet surface area; but not causing significant increases in vigor, weight, or chlorophyll content. In contrast, LS213 treatment resulted in significant increases, relative to the control, for all of these parameters. Similarly on cucumber (Table 4), LS213 caused significant increases in all parameters, compared both to the nontreated control and chitin alone.

B. Induced Resistance

After making the growth measurements described above, plants from three treatments of tomato and cucumber were transplanted to pots. Treatments tested were the nontreated control, chitin alone, and LS213. Tomato plants were inoculated with the tomato spot pathogen (as described in example 1B), and cucumber plants were inoculated with *Pseudomonas syringae* pv. lachrymans, causal agent of angular leaf spot disease. The results are shown in Table 5.

The results shown in Table 5 indicate that seedlings prepared from LS213 treatments had induced disease resistance. Interestingly, the seedlings prepared from treatment with chitin alone, which caused some significant plant growth increases, were not resistant. The lack of induced resistance with chitin when significant growth promotion occurred further demonstrates that the benefits of LS213 are synergistic.

TABLE 3

Results of Example 2A-growth promotion of tomato-synergy of tactics.

| Treatments and components[1] | Vigor[2] | Height (cm)[3] | Weight (g)[4] | Number of leaflets[5] | Leaflet surface area (cm$^2$)[6] | Chlorophyll[7] |
|---|---|---|---|---|---|---|
| Control; no components | 1.5 a | 7.0 a | 0.19a | 4.2 a | 1.64a | 28.09 a |
| LS213; chitin + GB03 + IN937a | 4.5 c | 13.31d | 0.91d | 9.6 d | 5.77c | 32.36 c |
| Chitin | 2.3 a | 10.7 c | 0.71a | 8.9 cd | 3.89c | 28.89 ab |
| Chitin + GB03 | 2.8 b | 10.83c | 0.72c | 8.9 cd | 4.09c | 32.54 c |
| Chitin + IN937a | 2.8 b | 11.03c | 0.74c | 8.9 cd | 4.75d | 31.39 bc |
| GB03 | 1.8 a | 7.40a | 0.23a | 4.6 a | 1.80a | 28.64 ab |
| IN937a | 2.8 b | 8.80b | 0.36b | 5.8 b | 2.68b | 28.17 a |
| GB03 + IN937a | 1.5 a | 7.33a | 0.25a | 4.7 a | 1.78a | 30.58abc |
| LSD (0.05) | 0.86 | 0.71 | 0.07 | 0.70 | 0.56 | 2.86 |

[1]Biological treatments were incorporated into soil-less mix at 1:40 (v/v) and placed into Styrofoam transplant flats and then seeded with tomato cv. Solar Set. There were four replicated flats per treatment.
[2]Seedling vigor was rated at 3 weeks after seeding on a scale of 1–5; 1 = poor, 2 = average, 3 = good, 4 = very good and 5 = excellent. Mean of four replication.
[3]Seedling height from the soil level to the tip. Mean of 4 replications, 5 seedlings per replication.
[4]Seedling shoot fresh weight. Mean of 4 replications, 5 seedlings per replication.
[5]Number of leaflets per plant. Mean of 4 replications, 5 plants per replication.
[6]Largest leaflet surface area (usually from the 4rth or 5$^{th}$ true leaf). Mean of 4 replications, 5 plants per replication.
[7]Chlorophyll content from the largest leaflet either from 4rth or 5$^{th}$ true leaf. Mean of 4 replications, 5 plants per replication.
Means followed by different letters are significantly different according to the protected least significance difference (LSD) test at P = 0.05.

TABLE 4

Results of Example 2A-growth promotion of cucumber-synergy of tactics.

| Treatments and components[1] | Vigor[2] | Height (cm)[3] | Weight (g)[4] | No. leaves[5] | Leaf area (cm$^2$)[6] | Chlorophyll[7] |
|---|---|---|---|---|---|---|
| Control; no components | 1.8 a | 9.13a | 1.39 a | 1.9 ab | 13.99a | 22.99 a |
| LS213; chitin + GB03 + IN937a | 4.8 d | 16.28e | 2.97 c | 2.8 d | 27.68d | 29.72 e |
| Chitin alone | 2.3 ab | 14.65d | 2.23 d | 2.1 c | 24.62c | 25.22bcd |
| Chitin + GB03 | 2.8 bc | 12.33c | 1.93bc | 2.1 bc | 20.89b | 26.49 cd |
| Chitin + IN937a | 2.8 bc | 13.05c | 2.12cd | 2.1 c | 21.28b | 26.86 cd |
| GB03 | 1.5 a | 8.80a | 1.40 a | 1.9 ab | 13.60a | 23.01 a |
| IN937a | 3.5 c | 12.88c | 1.97bc | 2.0 abc | 18.47b | 24.07 ab |
| GB03 + IN937a | 1.8 a | 9.2 a | 1.42 a | 1.8 a | 13.80a | 23.14 a |
| LSD (0.05) | 0.86 | 1.23 | 0.25 | 0.21 | 2.81 | 1.67 |

[1]Biological treatments were incorporated into soil-less mix at 1:40 (v/v) and placed into Styrofoam transplant flats and then seeded with tomato cv. Solar Set. There were four replicated flats per treatment.
[2]Seedling vigor was rated at 3 weeks after seeding on a scale of 1–5; 1 = poor, 2 = average, 3 = good, 4 = very good and 5 = excellent. Mean of four replication.
[3]Seedling height from the soil level to the tip. Mean of 4 replications, 5 seedlings per replication.
[4]Seedling shoot fresh weight. Mean of 4 replications, 5 seedlings per replication.
[5]Number of leaflets per plant. Mean of 4 replications, 5 plants per replication.
[6]Largest leaf surface area (usually from the 4rth or 5$^{th}$ true leaf). Mean of 4 replications, 5 plants per replication.
[7]Chlorophyll content from the largest leaf either from 4rth or 5$^{th}$ true leaf. Mean of 4 replications, 5 plants per replication.
Means followed by different letters are significantly different according to the protected least significance difference (LSD) test at P = 0.05.

TABLE 5

Results of Example 2B-induced resistance on tomato and cucumber-synergy of tactics

| Treatment[1] | Tomato/Xanthomonas axonopodis pv. vesicatoria[2] | Cucumber/Pseudomonas syringae pv. lachrymans[3] |
|---|---|---|
| Control | 18.97b | 18.45b |
| Chitin | 17.63b | 17.90b |
| LS213 | 7.87a | 10.80a |
| LSD (P = 0.05) | 3.04 | 3.23 |

[1]Biocontrol products applied as soil amendments prior to seeding.
[2]Values for X. axonopodis pv. vesicatoria represent the mean number of lesions per leaflet of each tomato seedling from four replications, 5 plants per replication per treatment.
[3]Values for P. syringae pv. lachrymans represent the mean number of total leaf spot symptoms per leaf from four replications, 5 plants per replication per treatment.

EXAMPLE THREE

Synergy of Tactics Multiple Crops, Growth Promotion

An example was conduced to determine if the synergistic effects on seeding plant growth noted in examples 1 and 2 occurred with additional crops. In this experiment, a nontreated control, chitin alone, LS213 treatments were preparedas described in example 1 and used to grow seedlings of tomato (cv. Solar Set), cucumber (cv. SMR 48), bell pepper (cv. California Wonder), and tobacco (cv. TN90). Seedling growth was monitored by measuring the parameters listed in Table 6. With tomato and cucumber, the results previously seen repeated in which LS213 treatment generally resulted in significant growth promotion compared both to the nontreated control and the treatment with chitin alone (Table 6). This synergistic effect on growth was seen with pepper and and tobacco.

EXAMPLE FOUR

Different Mixtures of PGPR with Chitin

An experiment was conducted to determine if one of the PGPR strains used in LS213 could be replaced with another strain. More specifically, PGPR strain IN937a from LS213 was replaced with 8 differnt bacilli, each of which had induced resistance activity by itself. The bacteria were mixed with PGPR strain GB03 and chitin prior to incorporating into soil-less plant growth medium. Effects on seedling growth of cherrry tomato (cv. RX335) were tested along with effects on induced resistance against bacterial spot. Results shown in Table 7 show that LS213 caused significant promotion of plant growth and induction of resistance, compared to the control with this cultivar of tomato similar to what was seen previously on 'Solar Set' tomato. Other combinations of bacteria and chitin generally caused significant enhancements in growth compared to the control; however, not all of these caused significant protection against bacterial spot. Overall the results show that the beneficial effects of the invention are bacterial-strain dependent, but that differnt mixtures of bacteria may be used to achieve the same results.

TABLE 6

Results of Example 3-synergy of tactics on multiple crops

| Treatments[1] | Healthy stand[2] | Vigor[3] | Height (cm)[4] | Number of leaves[5] | Shoot fresh weight (g)[6] | Leaf surface area (cm2)[7] |
|---|---|---|---|---|---|---|
| Tomato | | | | | | |
| Control | 22.5 a | 1.0 a | 4.68 a | 2.3 a | 0.079a | 0.69 a |
| Chitin | 22.0 a | 2.3 b | 6.98 b | 7.1 b | 0.266b | 1.65 b |
| LS213 | 23.0 a | 3.3 c | 9.03 c | 8.5 c | 0.539c | 3.03 c |
| LSD (P = 0.05) | 2.73 | 0.51 | 0.719 | 0.77 | 0.103 | 0.45 |
| Cucumber | | | | | | |
| Control | 22.3 a | 1.0 a | 4.35 a | 2.0 a | 0.709a | 5.56 a |
| Chitin | 23.8 b | 1.3 a | 4.58 ab | 2.1 a | 0.927a | 7.49 b |
| LS213 | 23.3 a | 2.5 b | 6.40 c | 2.2 a | 1.351b | 14.20 c |
| LSD (P = 0.05) | 1.22 | 0.49 | 0.704 | 0.29 | 0.304 | 2.89 |
| Pepper | | | | | | |
| Control | 18.5 a | 1.0 a | 3.30 a | 2.0 a | 0.054a | 0.21 a |
| Chitin | 20.0 a | 1.8 b | 3.78 b | 4.2 b | 0.163b | 1.43 b |
| LS213 | 20.0 a | 3.3 c | 4.83 c | 4.4 b | 0.299c | 2.64 c |
| LSD (P = 0.05) | 3.48 | 0.69 | 0.39 | 0.41 | 0.052 | 0.364 |
| Tobacco | | | | | | |
| Control | 21.5 a | 2.5 a | 0.1 a | 1.0 a | 0.002a | 0.01 a |
| Chitin | 17.0 a | 2.0 a | 0.98 b | 3.1 b | 0.079b | 1.37 b |
| LS213 | 21.5 a | 4.0 b | 1.8 c | 4.0 c | 0.169c | 3.22 c |
| LSD (P = 0.05) | 4.96 | 0.8 | 0.32 | 0.45 | 0.047 | 0.736 |

Biological treatments were incorporated into soil-less mix at 1:40 (v/v). There were four replicated flats per treatment.
[2]Seedling stand was rated at 3 weeks after seeding. Values represent mean of 4 replications per treatment.
[3]Seedling vigor was rated at 3 weeks after seeding on a scale of 1–5; 1 = poor, 2 = average, 3 = good, 4 = very good and 5 = excellent. Mean of four replication.
[4]Seedling height from the soil level to the tip. Mean of 4 replications, 5 seedlings per replication.
[5]Seedlings shoot fresh weight. Mean of 4 replications, 5 seedlings per replication.
[6]Number of leaves per plant. Mean of 4 replications, 5 plants per replication.
[7]Largest leaf surface area (usually from the 4th or 5th true leaf). Mean of 4 replications, 5 plants per replication.

TABLE 7

Results of Example 4-Different mixtures of PGPR with Chitin

| Treatments; components[1] | Vigor[2] | Height (cm)[3] | Number of leaflets[4] | Stem diameter (mm)[5] | Shoot fresh weight (g)[6] | Leaflet surface area (cm²)[8] | Induced resistance; No. bacterial spot lesions per leaflet |
|---|---|---|---|---|---|---|---|
| LS254; chitin + GB03 + SE34 | 2.5 a | 9.64 c | 19.1bc | 1.99cd | 0.709cd | 2.46 b | 12.2 cd |
| LS255; chitin + GB03 + IN937b | 3.5 bc | 9.58 c | 20.1 c | 2.02cd | 0.651bc | 2.33 b | 10.6 c |
| LS256; chitin + GB03 + INR7 | 4.0 bcd | 11.89de | 21.5 c | 2.14cd | 0.946 e | 3.49 c | 9.5 bc |
| LS257; chitin + GB03 + T4 | 3.5 bc | 13.23 f | 21.4 c | 2.38 d | 0.984 e | 3.42 c | 4.6 ab |
| LS258; chitin + GB03 + IPC11 | 2.5 ab | 10.01 c | 22.2 c | 2.19cd | 0.884de | 3.03 c | 17.8 d |
| LS259; chitin + GB03 + IPN19 | 2.0 a | 7.65bc | 16.9 b | 1.64 b | 0.502bc | 2.10 b | 9.4 bc |
| LS260; chitin + GB03 + 3P114 | 2.5 ab | 9.24 c | 19.9 c | 2.10cd | 0.721cd | 2.14 b | 10.3 bc |
| LS261; chitin + GB03 + C1 | 4.5 cd | 10.99cd | 20.9 c | 2.28 d | 0.869de | 3.52 c | 3.3 a |
| LS213; chitin + GB03 + IN937a | 5.0 d | 12.43 ef | 22.0 c | 2.46 d | 1.033 e | 3.36 c | 3.9 ab |
| Nontreated control | 1.5 a | 4.13 a | 5.9 a | 1.10 a | 0.085 a | 0.36 a | 12.7 cd |
| LSD (P = 0.05) | 1.32 | 1.31 | 2.8 | 0.28 | 0.186 | 0.568 | 5.69 |

[1]Biological treatments were incorporated into soil-less mix) at 1:40 (v/v) and placed into Styrofoam transplant flats and then seeded with tomato cv. Cherry RX 335. There were two replicated flats per treatment.
[2]Seedling vigor was rated at 4 weeks after seeding on a scale of 1–5; 1 = poor, 2 = average, 3 = good, 4 = very good and 5 = excellent. Mean of 2 replications.
[3]Seedling height from the soil level to the tip. Mean of 2 replications, 10 seedlings per replication.
[4]Number of leaflets per plant. Mean of 2 replications, 10 leaflets per replication.
[5]Stem diameter is the mean of 2 replications, 10 seedlings per replication.
[6]Seedling shoot fresh weight. Mean of 2 replications, 10 seedlings per replication.
[7]Largest leaflet surface area (usually from the 4rth or $5^{th}$ true leaf). Mean of 2 replications, 10 leaflets per replication.
Means followed by different letters are significantly different according to the protected least significance difference (LSD) test at P = 0.05.

EXAMPLE FIVE

Field Trial on Tomato Protection Against Multiple Diseases

Two of the biological preparations used in Example 4 (LS213 and LS254) were tested in a field trial. The tomato seedlings (cv. 'Solar Set') were prepared as previously described by growing in soil-less mix trated with the biological preparations. A nontreated control group of plants was also prepared. The transplants were placed into a randomized complete block design, with 10 plants per replication and 5 replications of each treatment. The experiment was planted four times for assessment of 1) root-knot nematodes, 2) Fusarium crown and root rot with methyl bromide fumigation of soil, 3) Fusarium crown and root rot without soil fumigation, and 4) bacterial spot. Results, shown in Table 8, demonstrate that the biological preparations led to reduced develpment of all the tested diseases under field conditions.

EXAMPLE SIX

Field Trial on Tomato
Effect of Differnt Bacterial Mixtures with and Without Foliar Spray Two field trials were conducted on tomato to determine if different forms of the biological preparation (differing in one of the bacterial components) would protect gainst root-knot nematodes and bacterial spot as did tratment with LS213 in Example 5. Results, shown in Table 9, indicaate that other forms of thee biological preparation did lead to protection of plants against the two tested pathogens.

An objective was to determine if beneficial effects of the biological treatment could be enhanced by combining the standard treatment of the sil-less planting medium with a mid-season foliar spray of the bacterial components of the biological preparation. The results indicate that there was some additional protection seen by combining the standard treatment with a foliar spray. For example, without the foliar spray, LS254 caused significant protection against root-knot nematode but not against bacterial spot, while with the foliar spray, protection occurred against both pathogens.

EXAMPLE SEVEN

Field Trial on Cucumber

Effect of Differnt Bacterial Mixtures with and Without Foliar Spray

Similar to Example 6, two field trials were conducted on cucumber to assess disease control activity of different forms of the biological preparation with and without foliar sprays. The diseases were both naturally occurring-root-knot nematodes and anthracnose, a foliar fungal disease. The results presentd in Table 10 demonstrate that changing PGPR strain IN937a with different PGPR can result in disease protection activtiy in the field. The results also demonstrate that the beneficial effects of the biological preparations are not limited to a single cultivar of cucumber, since some reductions in incidence of both root-knot nematodes and anthracnose occurred on each cultivar tested.

A comparison of results in Table 10 from the field with and without foliar spray demonstrate that this "booster" tratment of the same PGPR contained in the biological preparation used in the soil-less seeding mix provides additional efficacy for disease protection. This can be seen by comparisons of the frequency of significant

TABLE 8

Results of Example 5, field trial on tomato

| | BIOLOGICAL CONTROL ACTIVITY AGAINST[a] | | | | | | |
|---|---|---|---|---|---|---|---|
| | Root-knot nematode[b] | | Fusarium crown rot[b] | | | Bacterial spot | |
| | no. plants | root- | | without MeBr | | no. of | mean |
| Treatment | with severe symptoms[c] | knot index[d] | with MeBr[e] FORL index[f] | no. of plants with symptoms | FORL index[f] | fruit with symptoms[g] | no. of spots/leaf[h] |
| Control | 4.2 | 8.0 | 1.5 | 8.0 | 1.3 | 11.3 | 58.5 |
| LS213 | 2.6 | 7.2 | 0.9 | 0.6 | 0.6 | 4.0 | 25.1 |
| LS254 | 0.8 | 4.4 | 1.0 | 0.8 | 0.8 | 5.7 | 20.2 |
| LSD$_{0.05}$ | 1.6 | 1.4 | 0.4 | 0.7 | 0.7 | 2.6 | 9.4 |
| LSD$_{0.10}$ | 1.4 | 1.2 | 0.3 | 0.6 | 0.6 | | |

[a]Experiment was a randomized complete block with 5 replications of each treatment; 10 plants per replication.
[b]Values shown are means of 9 root systems at harvest time.
[c]Severe symptoms were determined by the presence of large, coalescent galls in most of the root system.
[d]Root-knot index was based on a scale from 0 (no galls) to 10 (completely galled with poor root system).
[e]MeBr = methyl bromide.
[f]Fusarium crown and root rot index was determined using a scale of 0 (no symptoms) to 3 (severe and extended discoloration).
[g]No. of green tomato fruit (out of 20 picked per plot) with 2 or more lesions.
[h]Based on 10 leaves collected per plot.

TABLE 9

Results of Example 6-Field trial on tomato;
Effect of different bacterial mixtures with and without foliar spray.

| Treatments; components used in seedling mix | Additional foliar spray of PGPR (+ or −) | Severity of root-knot nematode[1] | Severity of bacterial spot per leaf[2] |
|---|---|---|---|
| LS254; chitin + GB03 + SE34 | + | 3.85* | 3.54* |
| LS255; chitin + GB03 + IN937b | + | 4.0* | 5.06 |
| LS257; chitin + GB03 + T4 | + | 3.92* | 4.22* |
| Nontreated control | + | 5.47 | 5.82 |
| LS254; chitin + GB03 + SE34 | − | 2.77* | 4.03 |

TABLE 9-continued

Results of Example 6-Field trial on tomato;
Effect of different bacterial mixtures with and without foliar spray.

| Treatments; components used in seedling mix | Additional foliar spray of PGPR (+ or -) | Severity of root-knot nematode[1] | Severity of bacterial spot per leaf[2] |
|---|---|---|---|
| LS255; chitin + GB03 + IN937b | – | 3.38* | 3.61* |
| LS257; chitin + GB03 + T4 | – | 3.36* | 3.43* |
| Nontreated control | – | 4.60 | 4.54 |

[1]Mean of 3 replications, 3–5 plants per replication. Root-knot severity was measured on a 0–10 scale per entire root system; 0 = no galls; 10 = total galling.
[2]Mean of 3 replications, 10–15 leaves per replication. Bacterial spot was assessed on a 0–10 scale; 0 = no lesions; 10 = maximum lesions.
*Indicates significantly different from the appropriate control at P = 0.05.

TABLE 10

Results of Example 7-Field trial on cucumber;
effect of different bacterial mixtures with and without foliar spray

| Treatment; Components used in soil-less mix | cv. Straight-8 | | cv. Fancypak | |
|---|---|---|---|---|
| | Root-knot[1] | % Anthracnose[2] | Root-knot[1] | % Anthracnose[2] |
| Without foliar spray | | | | |
| LS213; chitin + GB03 + IN937a | 2.92* | 17 | 1.85* | 27 |
| LS254; chitin + GB03 + SE34 | 2.77* | 20 | 1.46* | 27 |
| LS255; chitin + GB03 + IN937b | 2.21* | 13 | 0.82* | 20 |
| LS258; chitin + GB03 + IPC11 | 3.79 | 20 | 0.92* | 37 |
| LS260; chitin + GB03 + 3P114 | 2.46* | 23 | 2.67* | 13* |
| Control | 5.0 | 30 | 4.3 | 43 |
| With foliar spray | | | | |
| LS213; chitin + GB03 + IN937a | 4.79 | 17* | 0.83* | 17* |
| LS254; chitin + GB03 + SE34 | 5.43 | 3* | 1.00* | 27* |
| LS255; chitin + GB03 + IN937b | 2.70* | 13* | 2.00 | 17* |
| LS258; chitin + GB03 + IPC11 | 3.80 | 20* | 1.00* | 37* |
| LS260; chitin + GB03 + 3P114 | 3.08* | 17* | 0.83* | 17* |
| Control | 4.87 | 53 | 2.89 | 50 |

[1]Mean of 3 replications, 3–5 plants per replication.
[2]Mean of 3 replications, 3–5 plants per replication.
*Significantly different from control at P = 0.05.

disease reduction for one treatment with and without foliar spray. For example, with LS213, with foliar spray, 3 of the 4 disease incidence means were significantly reduced compared to the control, while without foliar spray, 2 of the 4 means were significantly reduced. With LS260, this "frequency of significance" increased from 2 of 4 without foliar spray to 4 of 4 with foliar spray.

It will be understood that many variations can be made in the procedures described for the composition, the methods and the plant products of the present invention while still remaining within the bounds and the spirit of the invention.

BIBLIOGRAPHY

Bauske, E. M., Backman, P. A., Harper, K. M., Brannen, P. M., Rodríguez-Kábana, R., and Kloepper, J. W. 1997. Effect of botanical aromatic compounds and seed-surface pH on growth and colonization of cotton plant growth-promoting rhizobacteria. *Biocontrol Science and Technology* 7, 415–421.

Bauske, E. M., Rodríguez-Kábana, R., Esaun, V., Kloepper, J. W., Robertson, D. G., Weaver, C. F., and King, P. S. 1994. Management of *Meloidogyne incognita* on cotton by use of botanical aromatic compounds. *Nematropica* 24:143–150.

Becker, J. O., Zavaleta-Meija, E., Colbert, S. F., Schroth, M. N., Weinhold, A. R., Hancock, J. G., and Van Gundy, S. D. 1988. Effects of rhizobacteria on root-knot nematodes and gall formation. *Phytopathology* 78:1466–1459.

Benhamou, N., Lafontaine, P. J. and Nicole, M. (1994) Induction of systemic resistance to Fusarium crown and root rot in tomato plants by seed treatment with chitosan. *Phytopathology* 84, 1432–1444.

Bird, A. F. and Bird, J. (1991) *The Structure of Nematodes*. Academic Press, San Diego.

Canullo, G., C., Rodríguez-Kábana, R., and Kloepper, J. W. 1992. Changes in soil microflora associated with control of *Sclerotium rolfsii* by furfuraldehyde. Biocontrol Science and Technology 2:159–169.

Ciancio, A. 1995. Density-dependent parasitism of *Xiphinema diversicaudatum* by *Pasteuria penetrans* in a naturally infested field. Phytopathology 85:144–149.

Culbreath A. K., Rodríguez-Kábana, R. and Morgan-Jones, G. (1985) The use of hemicellulosic waste matter for reduction of the phytotoxic effects of chitin and control of root-knot nematodes. *Nematropica* 15, 49–75.

Glick, B. R., and Bashan, Y. 1997. Genetic mainpulation of plant growth-promoting bacteria to enhance biocontrol of phytopathogens. *Biotechnology Advances* 15, 353–378.

Godoy, G., Rodríguez-Kábana, R., Shelby, R. A. and Morgan-Jones, G. (1983) Chitin amendments for control of *Meloidogyne arenaria* in infested soil. II. Effects on microbial population. *Nematropica* 13, 63–74.

Hallmann, J., Rodríguez-Kábana, R., and Kloepper, J. W. 1998. Chitin-mediated changes in bacterial communities of the soil, rhizosphere and within roots of cotton in relation to nematode control. *Soil Biology and Biochemistry* In press.

Hallmann, J., Rodríguez-Kábana, R., and Kloepper, J. W. 1997. Nematode interactions with endophytic bacteria. pp. 243–245 in: *Plant Growth-Promoting Rhizobacteria—Present Status and Future Prospects.* Eds. A. Ogoshi, K. Kobayashi, Y. Homma, F. Kodama, N. Kondo, and S. Akino. Nakanishi Publishing, Sapporo.

Inbar, J. and Chet, I. (1991) Evidence that chitinase produced by *Aeromonas caviae* is involved in the biological control of soil-borne plant pathogens by this bacterium. *Soil Biology and Biochemistry* 23, 973–978.

Kerry, B. R. (1982) The decline of *Heterodera avenae* populations. *European Plant Protection Organization Bulletin* 12, 491–496.

Kloepper, J. W. 1993. Plant growth-promoting rhizobacteria as biological control agents. In 'Soil Microbial Ecology—Applications in Agricultural and Environmental Management,' ed. F. B. Metting, Jr., pp. 255–274 (Marcel Dekker, Inc., New York).

Kloepper, J. W., Rodríguez-Kábana, R., McInroy, J. A., and Young, R. W. 1992. Rhizosphere bacteria antagonistic to soybean cyst (*Heterodera glycines*) and root-knot (*Meloidogyne incognita*) nematodes: Identification by fatty acid analysis and frequency of biological control activity. Plant and Soil 139:75–84.

Kluepfel, D. A., McInnis, T. M. and Zehr, E. I. (1993) Involvement of root-colonizing bacteria in peach orchard soils suppressive of the nematode *Criconemella xenoplax*. *Phytopathology* 83, 1240–1245.

Kokalis-Burelle, N., Rodríguez-Kábana, R., Weaver, C. F. and King, P. S. (1994) Evaluation of powdered pine bark for control of *Meloidogyne arenaria* and *Heterodera glycines* on soybean. *Plant and Soil* 162, 163–168.

Kokalis-Burelle, N., Rodríguez-Kábana, R., Robertson, D. G., Mahaffee, W. F., Kloepper, J. W. and Bowen, K. L. (1995) Effects of forage grass rotations on soil microbial ecology and nematode populations. *Phytopathology* 85, 1124.

Kuć, J. 1982. Induced immunity to plant disease. Bioscience 32:854–60.

Liu, L., Kloepper, J. W., and Tuzun, S. 1995a. Induction of systemic resistance in cucumber against bacterial angular leaf spot by plant growth-promoting rhizobacteria. Phytopathology 85:843–847.

Liu, L., Kloepper, J. W., and Tuzun, S. 1995b. Induction of systemic resistance in cucumber by plant growth-promoting rhizobacteria: duration of protection and effect of host resistance on protection and root colonization. Phytopathology 85:1064–1068.

Liu, L., Kloepper, J. W., and Tuzun, S. 1995c. Induction of systemic resistance in cucumber against Fusarium wilt by plant growth-promoting rhizobacteria. Phytopathology 85:695–698.

Mankau, R. and Das, S. (1969) The influence of chitin amendments on *Meloidogyne incognita*. *Journal of Nematology* 1, 15–16.

Martinez-Ochoa, N., Kloepper, J. W., Rodríguez-Kábana, R., and Ji, P. 1997. Induced resistance and phenotypic characteristics of several PGPR compared to biocontrol activity against the root knot nematode *Meloidogyne incognita*. pp. 296–300 in: *Plant Growth-Promoting Rhizobacteria—Present Status and Future Prospects.* Eds. A. Ogoshi, K. Kobayashi, Y. Homma, F. Kodama, N. Kondo, and S. Akino. Nakanishi Publishing, Sapporo.

Mercer, C. F., Greenwood, D. R. and Grant, J. L. (1992) Effect of plant and microbial chitinases on the eggs and juveniles of *Meloidogyne hapla* Chitwood. *Nematologica* 8, 227–236.

Mian, I. H., Godoy, G., Shelby, R. A., Rodríguez-Kábana, R. and Morgan-Jones, G. (1982) Chitin amendments for control of *Meloidogyne arenaria* in infested soil. *Nematropica* 12, 71–84.

Mitchell, R. and Alexander, M. (1962) Microbiological processes associated with the use of chitin for biological control. *Soil Science Society of America, Proceedings* 26, 556–558.

Oka, Y., Chet, I., and Spiegel, Y. 1993. Control of the rootknot nematode *Meloidogyne javanica* by *Bacillus cereus*. Biocontrol Science and Technology 3:115–126.

Ordentlich, A., Elad, Y. and Chet, I. (1988) The role of chitinase of *Serratia marcescens* in biocontrol of *Sclerotium rolfsii*. *Phytopathology* 78, 84–88.

Press, C. M., Wilson, M., Tuzun, S., Kloepper, J. W. 1997. Salicylic acid produced by *Serratia marcescens* 90–166 is not the primary determinant of induced systemic resistance in cucumber or tobacco. Molec. Plant-Microbe Interactions 10:761–768.

Raupach, G. S., Liu, L., Murphy, J. F., Tuzun, S., and Kloepper, J. W. 1996. Induced systemic resistance in cucumber and tomato against cucumber mosaic cucumovirus using plant growth-promoting rhizobacteria (PGPR). Plant Dis. 80:891–894.

Punja, Z. K. and Zhang, Y. -Y. (1993) Plant chitinases and their roles in resistance to fungal diseases. *Journal of Nematology* 25, 526–540.

Roberts, C. A., Marek, S. M., Niblack, T. L. and Karr, A. L. (1992) Parasitic Meloidogyne and mutualisitc Acremonium increase chitinase in tall fescue. *Journal of Chemical Ecology* 18, 1107–1116.

Rodríguez-Kábana, R., Godoy, G., Morgan-Jones, G. and Shelby, R. A. (1983) The determination of soil chitinase activity: Conditions for assay and ecological studies. *Plant and Soil* 75, 95–106.

Rodríguez-Kábana, R., Kloepper, J. W., Weaver, C. F., and Robertson, D. G. 1993. Control of plant parasitic nematodes with furfural—a naturally occurring fumigant. Nematropica 23:63–73.

Rodríguez-Kábana, R. and Morgan-Jones, G. (1987) Biological control of nematodes: Soil amendments and microbial antagonists. *Plant and Soil* 100, 237–247.

Rodríguez-Kábana, R., Morgan-Jones, G. and Gintis, B. O. (1984) Effects of chitin amendments to soil on *Heterodera glycines*, microbial populations, and colonization of cysts by fungi. *Nematropica* 14, 10–25.

Ross, A. F. 1961. Systemic acquired resistance induced by localized virus infection in plants. Virology 14:340–58.

Ryals, J., Neuenshwander, U. H., Willits, M. G., Molina, A., Steiner, H. Y., et al. 1996. Systemic acquired resistance. Plant Cell 8:1809–19.

Sikora, R. A. 1988. Interrelationship between plant health promoting rhizobacteria, plant parasitic nematodes and soil microorganisms. Med. Fac. Landouww. Rijksuniv. Gent 53:867–878.

Soler-Serratosa, A., Kokalis-Burelle, Rodríguez-Kábana, R., Weaver, C. F., and King, P. S. 1996. Allelochemicals for control of plant-parasitic nematodes. 1. in vivo nematicidal efficacy of thymol and thymol/benzaldehyde combinations.

Soler-Serratosa, A., Rodríguez-Kábana, R., and Kloepper, J. W. 1994. Selective enrichment of Pseudomonas spp. in soils treated with thymol for control of phytoparasitic nematodes. In: M. H. Ryder, P. M. Stevens, and G. D. Bowen, eds. Improving Plant Productivity with Rhizobacteria. CSIRO Press, Adelaide, Australia., p. 198.

Spiegel, Y., Cohn, E. and Chet, I. (1986) Use of chitin for controlling plant-parasitic nematodes. I. Direct effects on nematode reproduction and plant performance. *Plant and Soil* 95, 87–95.

Sticher, L., Mauch-Mani, B. Métraux, J. P. 1997. Systemic acquired resistance. Annu. Rev. Phytopathol. 35:235–70.

Stirling, G. R. 1991a. Mass production and release of biological control agents. Chapter 6 in: *Biological Control of Plant Parasitic Nematodes—Progress, Problems and Prospects*. CAB International, Wallingford, Oxon, UK.

Stirling, G. R. 1991b. Naturally occurring biological control. Chapter 5 in: *Biological Control of Plant Parasitic Nematodes—Progress, Problems and Prospects*. CAB International, Wallingford, Oxon, UK.

Stirling, G. R., McKenry, M. V. and Mankau, R. (1979) Biological control of root-knot nematodes (Meloidogyne spp.) on peach. *Phytopathology* 69, 806–809.

Van Loon, L. C., 1997. Induced resistance in plants and the role of pathogenesis-related proteins. Eur. J. Plant Pathol. 103:753–65.

Van Loon, L. C., Bakker, P. A. H. M., and Pieterse, C. M. J. 1998. Systemic resistance induced by rhizosphere bacteria. Annu. Rev. Phytopathol. 36:453–83.

Vargas, R., Rodríguez-Kábana, R. and Kloepper, J. W. (1994) Study of microbial ecology in a crop rotation program with soybean, velvetbean, and winter crops. *Phytopathology* 84, 1084.

Wei, G., Kloepper, J. W., and Tuzun, S. 1996. Induced systemic resistance to cucumber diseases and increased plant growth by plant growth-promoting rhizobacteria under field conditions. Phytopathology 86:221–224.

Yao, C. -B., Zehner, G. W., Sikora, E., Murphy, J., and Kloepper, J. W. 1997. Evaluaution of induced systemic resistance and plant growth promotion in tomato with selected PGPR strains. In 'Plant Growth-Promoting Rhizobacteria—Present Status and Future Prospects,' eds. A. Ogoshi, K. Kobayashi, Y. Homma, F. Kodama, N. Kondo, and S. Akino, pp. 285–288. (Nakanishi Printing, Sapporo).

Zehnder, G., Kloepper, J., Tuzun, S., Yao, C. Wei, G., Chambliss, O., and Shelby, R. 1997a. Insect feeding on cucumber mediated by rhizobacteria-induced plant resistance. Entomologia Experimentalis et Applicata 83:81–85.

Zehnder, G., Kloepper, J., Yao, C., and Wei, G. 1997b. Induction of systemic resistance in cucumber against cucumber beetles (Coleoptera: Chrysomelidae) by plant growth-promoting rhizobacteria). J. Econ. Entomol. 90:391–396.

What is claimed is:

1. A composition for affecting plant growth or imparting disease resistance, comprising at least one plant growth-promoting rhizobacteria (PGPR) and chitosan in an amount of at least 1%.

2. The composition of claim 1, wherein at least one PGPR is chitinolytic.

3. The composition of claim 1, wherein at least one PGPR is a spore-forming bacterium.

4. The composition of claim 1, wherein at least one PGPR is a non-spore forming bacterium.

5. The composition of claim 1, wherein chitosan is present in an amount of at least 2.5%.

6. The composition of claim 1, wherein at least one PGPR is non-chitinolytic.

7. The composition of claim 6, wherein at least one PGPR is selected from the family BACILLIACEAE.

8. The composition of claim 7, wherein the BACILLIACEAE PGPR is selected from the genera consisting of Bacillus, Paenibacillus, Brevibacillus, Virgibacillus, Alicyclobacillus and Aneurinibacillus.

9. The composition of claim 8, wherein the PGPR is selected from the following: *Bacillus subtilis, Bacillus subtilis* strain GB03, *Bacillus amyloliquefaciens*, and *Bacillus amyloliquefaciens* strain IN937a.

10. The composition of claim 7, wherein the composition comprises at least two different bacteria of the family BACILLIACEAE.

11. The composition of claim 10, wherein the bacteria are *Bacillus subtilis* strain GB03 and *Bacillus amyloliquefaciens* strain IN937a.

12. The composition of claim 6, wherein at least one PGPR comprises root-colonizing bacteria.

13. The composition of claim 12, wherein at least one PGPR is a root-colonizing bacteria selected form a fluorescent pseudomonad and isolates of Pseudomonas spp., Serratia spp., Corynebacterium spp., Enterobacter spp., Arthrobacter spp. and Burkholderia spp.

14. The composition of claim 1 wherein the composition further comprises at least one non-essential ingredient, which does not detrimentally affect the function of the PGPR or the chitosan.

15. The composition of claim 14, wherein the non-essential ingredient comprises at least one botanical aromatic compound.

16. The composition of claim 15, wherein the botanical aromatic compound is selected from the group of benzaldehyde, citral, thymol, furfural, menthol and alpha-terpineol.

17. A method for affecting at least plant growth or imparting disease resistance to plants or seeds comprising the steps of treating a seed or seedling of a target plant with a composition comprising at least one plant growth-promoting rhizobacteria (PGPR) and chitosan in an amount of at least 1%, and growing the treated seed or seedling.

18. The method of claim 17, wherein the method further comprises collecting a treated seed or seedling.

19. The method of claim 17, wherein the method further comprises transplanting a treated seed or seedling at least once.

20. The method of claim 17, wherein the method further comprises planting a treated seed or seedling into soil.

21. The method of claim 17 in which the composition is contained in a collectible container.

22. The method of claim 17 wherein the treatment is exposing the treated seed or seedling to the composition by foliar spray, drench, drip or irrigation treatment.

23. The method of claim 22, wherein the method comprises repeating the exposure.

24. The method of claim 17 wherein the treatment is exposing the untreated seed or seedling to the composition by a foliar spray, drench, drip or irrigation treatment.

25. The method of claim 17, wherein the method firer comprises coating an untreated seed with the composition comprising at least one plant growth-promoting rhizobacteria (PGPR) and chitosan in an amount of at least 1%, by exposing the untreated seed to the composition.

26. A coated seed treated according to the method of claim 17.

27. The seed of claim 26, having resistance to diseases, which are caused by plant pathogens, which diseases are selected from the group consisting of bacterial, fungal, viral, and nematode diseases.

28. The seed of claim 26, wherein the seed is from a plant species selected from the group consisting of a monocotyledonous and dicotyledonous plant species.

29. The coated seed of claim 26, which is planted in soil.

30. The treated seed of claim 26, treated with the composition by immersing, spraying, powdering, drenching, dripping, or irrigating an untreated seed.

31. The seed of claim 26, wherein the composition further comprises at least one non-essential ingredient, which does not detrimentally affect the function of the PGPR or the chitosan.

32. The seed of claim 31, wherein the non-essential ingredient comprises at least one botanical aromatic compound.

33. The seed of claim 32, wherein the botanical aromatic compound is selected from the group of benzaldehyde, citral, thymol, furfural, menthol and alpha-terpineol.

* * * * *

UNITED STATES PATENT AND TRADEMARK OFFICE
CERTIFICATE OF CORRECTION

PATENT NO. : 6,524,998 B1
DATED : February 25, 2003
INVENTOR(S) : Joseph W. Kloepper et al.

It is certified that error appears in the above-identified patent and that said Letters Patent is hereby corrected as shown below:

Title page,
Item [75], Inventors, correct to read:
-- Joseph W. Kloepper, Auburn, AL (US), Rodrigo Rodriguez-Kabana, Auburn, AL (US); Donald S. Kenney, Denton, TX (US); and Sadik Tuzun, Auburn, AL (US) --

Signed and Sealed this

Ninth Day of August, 2005

JON W. DUDAS
*Director of the United States Patent and Trademark Office*